(12) United States Patent
Balas

(10) Patent No.: US 7,749,162 B2
(45) Date of Patent: Jul. 6, 2010

(54) VAGINAL SPECULUM ARRANGEMENT

(75) Inventor: Constantinos Balas, Athens (GR)

(73) Assignee: Forth Photonics Ltd., London (GB)

( * ) Notice: Subject to any disclaimer, the term of this patent is extended or adjusted under 35 U.S.C. 154(b) by 454 days.

(21) Appl. No.: 11/540,334

(22) Filed: Sep. 29, 2006

(65) Prior Publication Data

US 2007/0135687 A1    Jun. 14, 2007

Related U.S. Application Data

(60) Provisional application No. 60/722,367, filed on Sep. 29, 2005.

(51) Int. Cl.
    *A61B 1/32*    (2006.01)
(52) U.S. Cl. .................. 600/221; 600/220; 600/229
(58) Field of Classification Search .......... 600/201, 600/219–221, 268, 225–229; 606/7, 14–17; 435/285.3; 604/109
    See application file for complete search history.

(56) References Cited

U.S. PATENT DOCUMENTS

| 3,789,829 | A |   | 2/1974 | Hasson |
| 4,807,600 | A | * | 2/1989 | Hayes ................. 600/203 |
| 5,458,595 | A |   | 10/1995 | Tadir et al. |
| 5,951,461 | A | * | 9/1999 | Nyo et al. ............. 600/118 |
| 6,361,991 | B1 | * | 3/2002 | Furth et al. ........... 435/285.3 |
| 6,432,048 | B1 | * | 8/2002 | Francois .............. 600/220 |
| 6,432,049 | B1 | * | 8/2002 | Banta et al. ........... 600/249 |
| 2002/0197728 | A1 |   | 12/2002 | Borodulin et al. |
| 2003/0207250 | A1 |   | 11/2003 | Kaufman et al. |
| 2003/0225313 | A1 |   | 12/2003 | Borodulin et al. |
| 2005/0090751 | A1 |   | 4/2005 | Balas |

FOREIGN PATENT DOCUMENTS

| FR | 2328440 | 6/1977 |
| WO | WO-93/19678 A2 | 10/1993 |
| WO | WO-2005/055819 A1 | 6/2005 |

OTHER PUBLICATIONS

European Search Report for Application No. 05386023.5-2305, dated May 9, 2006.
International Search Report for Application No. PCT/GB2006/003648, dated Mar. 14, 2007.

* cited by examiner

*Primary Examiner*—Eduardo C Robert
*Assistant Examiner*—Christina Negrelli
(74) *Attorney, Agent, or Firm*—Nixon & Vanderhye P.C.

(57) ABSTRACT

The present invention relates to a vaginal speculum embodying an applicator for the uniform delivery of a standardized dose of a liquid diagnostic marker onto the woman's lower genital tract. The applicator can comprises of a marker container and a mechanism for transferring a desirable quantity of its content to an injection probe for dispensing the marker onto the tissue surface. The cross section of the injection probe is substantially smaller than the rear opening of the speculum, so that the monitoring of the optical effects provoked to the tissue by the marker and the insertion of treatment tools is not obstructed.

32 Claims, 5 Drawing Sheets

VAGINAL SPECULUM ARRANGEMENT

RELATED APPLICATIONS

This application is related and claims priority to U.S. Provisional Application No. 60/722,367, filed Sep. 29, 2005. The disclosure of said Application is hereby incorporated by reference in its entirety.

FIELD OF THE INVENTION

The present invention relates to a vaginal speculum arrangement. More specifically, the present invention relates to a vaginal speculum arrangement that allows for the uniform delivery of a dose of a liquid diagnostic marker onto the woman's lower genital tract and provides a substantially unobstructed viewing arrangement to observe the effects of the marker.

BACKGROUND

Detection and identification of pathologic alterations of the woman's low genital track (cervix of the uterus, vagina) involves a series of medical procedures including screening tests (pap-test), tissue examination with the aid of a microscope (colposcopy), biopsy sampling and histology. An abnormal pap-test is followed by colposcopy, where the vagina is opened with the aid of a speculum to allow tissue visualization with the aid of a microscope. In colposcopy, a number of diagnostic markers are applied topically, which alter the optical properties of the tissue, depending on the pathology. Particularly, application of 3-5% acetic acid solution provokes a reversible whitening of the abnormal tissue areas. It has been proved that the degree and the duration of the whitening effect correlates well with the neoplasia grade. The provoked contrast enhancement between normal and abnormal areas provide a valuable means for assisting colposcopic diagnosis and for locating abnormal areas for biopsy sampling and treatment. There is a considerable confidence for the diagnostic value of these diagnostic markers, which has been developed during the 70 years usage of these tests in the clinical practice.

The employment of marker-based in vivo tests as an alternative to the in vitro pap test for screening cervical pathology has increased in recent years. Marker-based in vivo tests employ a procedure similar to the colposcopy procedure, but typically are performed without the use of a microscope (colposcope). The vagina is opened with the aid of a speculum, which is followed by the application of acetic acid solution onto tissue surface and naked-eye monitoring of the marker-induced alterations in the color of the examined tissue. This technique is known as speculoscopy. In contrast to the pap-test, speculoscopy offers diagnostic results immediately, which enable the biopsy sampling and/or the treatment of the lesion even during the same consultation.

One main drawback of both colposcopy and speculoscopy arises from the fact that the quantity of applied marker is not standardized, while the marker administration means and procedures do not ensure its uniform application over the entire area of the examined tissue. In addition, the injection means employed obstruct the rear opening of the speculum, not allowing the monitoring of the effects provoked by the marker during its application and due to this fact critical diagnostic information is missed. Typically, an uncontrolled volume of the marker is applied either by washing the tissue with the aid of a cotton brush, moistened with acetic acid solution, or with the aid of a general purpose, hand held atomizer, which delivers a random quantity of the marker remotely. In some cases more than one injection are performed in a repetitive manner during the evolution of the acetowhitening phenomenon in order to achieve better contrast.

Clinical research, conducted by the inventors of the present invention, has shown that the monitoring of the effects provoked by the marker, during and after its application, has a great diagnostic value. The same research has also shown that the concentration and the quantity of the marker solution, applied onto the examined tissue are very critical since for a given pathology, different marker doses generate different optical effects, which may cause misdiagnosis. Particularly, for a given tissue pathology, an insufficient marker dose may cause in cancerous lesions an acetowhitening pattern similar to the one provoked by an optimum marker quantity in inflammations and in low grade neoplasias. Similarly, a high marker dose can cause an acetowhitening pattern in inflammations and low grade precancerous lesions typically found in cancerous lesions. Consequently, the lack of an arrangement enabling the standardization of the marker quantity applied onto the tissue surface may result in false positive and/or false negative results, thus, diminishing the diagnostic performance of these tests in terms of both sensitivity and specificity.

A number of prior art documents disclose various speculum arrangements with imaging and illuminations means integrated with a speculum, but they are characterized by the lack of injection means for applying uniformly a standardized quantity of a diagnostic marker, while simultaneously allowing for the inspection of the optical effects produced by the latter.

Such prior art documents include GB214913 and GB191027965. These documents disclose a vaginal speculum with incorporated fluid injection means. The purpose of fluid injection means, as described in these documents, is for washing the woman's low genital tract and it does not offer any standardization of the injected liquid. It is worth noticing that in these prior art documents, washing does not employ a diagnostic marker and therefore it is not intended to assist diagnosis and screening. More importantly, it does not allow for the visualization of the area of interest, since the whole inner space of the speculum is occupied by the fluid injection means and no free space is available allowing observation and insertion of treatment tools.

Other prior art documents disclose vaginal specula with integrated illumination means for illuminating the vagina. Such specula are disclosed, e.g., in documents GB1408382, U.S. Pat. Nos. 3,762,400, 3,851,642. These vaginal specula are intended for the medical examination of the vagina, but they are not accompanied with integrated fluid injection means, necessary for a diagnostic medical examination of the vagina wherein the uniform application of a standard volume of a diagnostic marker is necessary.

Other prior art described in documents WO9007299, WO9728753, U.S. Pat. Nos. 4,210,133 and 4,046,140, discloses vaginal specula with an integrated microscope or camera for observing and/or for capturing images of the cervical tissue. In the described implementations the microscopes or cameras are located within the blades not allowing the insertion of tools for biopsy sampling and treatment simultaneously with the inspection with the aid of a microscope or camera. In addition, the instruments disclosed in the foregoing documents do not allow the injection of diagnostic markers. Finally, the prior art document US20040122327 discloses an uteroscope arrangement including a panoramic lens for viewing the entire uterine cavity in one image that is mounted on an elongated shaft for insertion into the patient's uterus. One or more transparent inflatable balloons are mounted on the elongated shaft surrounding the optical imaging system. An instrument channel is provided in the shaft of the uteroscope for insertion of instruments, such as a suction tube, external to or in between the transparent inflatable balloons.

SUMMARY OF THE INVENTION

The present invention relates to a vaginal speculum embodying an applicator for the uniform delivery of a standardized dose of a liquid diagnostic marker onto the woman's lower genital tract. The applicator comprises of a marker container and a mechanism for transferring a desirable quantity of its content to an injection probe for dispensing the marker onto the tissue surface. The injection probe may be a nozzle generating a desirable injection pattern, depending on the location of the tissues to be examined. The cross section of the injection probe is substantially smaller than the rear opening of the speculum, so that the monitoring of the optical effects provoked to the tissue by the marker and the insertion of treatment tools is not obstructed.

The probe may be affixed to an extension shaft, which may be mechanically coupled with the speculum blades, in such a way that the longitudinal axis of the probe and consequently the injection direction remains stable, independently from the actual opening angle of the blades, determined by the anatomy of the vaginal wall. Optical, electronic imaging means, illumination means and treatment tools may be mounted onto the extension shaft. The extension shaft may be detachably attached to mechanical positioning systems or to imaging devices used in colposcopy.

The disclosed speculum arrangement may be used as a tool for diagnostic and screening examinations and for the treatment of cervical and vaginal neoplasias.

In on aspect, a vaginal speculum arrangement is disclosed that includes a blade system and an injection mechanism. The blade system is provided for opening the vagina. The blade system includes a first blade and a second blade, where the first and second blades are positionable relative to each other at a multitude of angles and about a longitudinal symmetry axis extending between a distal portion and a proximate portion of each of the first and second blades. The injection mechanism dispenses a diagnostic marker onto a surface of examined tissue. The injection mechanism includes an injection probe that has a longitudinal axis, a marker container and an injector for enabling injection of the marker. The relative position of the longitudinal axis of the injection probe and the longitudinal symmetry axis of the blade system remain substantially fixed at each of a multitude of angles between the first and second blades. A cross section of the injection probe has dimensions that are substantially smaller than dimensions of a cross section of a rear aperture of the blade system. The injection probe allows for a substantially homogeneous application of the marker on a desired area of the examined tissue, irrespectively from an opening angle of the first and second blades and allows for observation of the desired area through the rear aperture of the blade system, before, during, and after the injection of the marker.

In another aspect, a vaginal speculum arrangement is disclosed that includes a blade system and a mechanical support. The blade system opens the vagina and includes a first blade and a second blade. The first and second blades are positionable relative to each other in a multitude of angles and along a longitudinal symmetry axis that extends between a distal portion and a proximate portion of each of the first and second blades. The mechanical support includes a shaft with a first shaft end mechanically coupled with the blade system and a second shaft end detachably coupled to another device. The first shaft end of the shaft is movably coupled with a blade-handle joint of the first blade and a pin of the blade-handle joint of the second blade moves within a groove, formed along a longitudinal axis of said extension shaft.

The object of the present invention is to provide a speculum arrangement, integrating means for dispensing uniformly a standardised marker volume, while simultaneously allowing for the visualization and monitoring of the provoked optical effects, for diagnostic and screening purposes and the insertion of treatment tools into the vaginal canal, for biopsy sampling and treatment.

It is another object of the present invention to provide a speculum arrangement further integrating optical, electronic imaging, and illumination means with a speculum arrangement embodying a diagnostic marker injection mechanism, while simultaneously allowing for the insertion of treatment tools into the vaginal canal.

It is still another object of the invention to provide a speculum arrangement with an extension shaft, which may be connected with a mechanical support and positioning means, including the ones employed in imaging devices used in colposcopy, for the support and stabilization of the speculum and hands free operation.

BRIEF DESCRIPTION OF THE DRAWINGS

The invention is pointed out with particularity in the appended claims. The advantages of the invention described above, as well as further advantages of the invention, may be better understood by reference to the following description taken in conjunction with the accompanying drawings, in which:

DETAILED DESCRIPTION OF THE INVENTION

A Cusco-type speculum is illustrated in the figures for illustrative purposes and those skilled in the art will appreciate the present invention is not limited to such a speculum, but rather is applicable to any kind of speculum having a mechanical arrangement suitable for opening the vagina to enable the visualization of the tissues composing a woman's lower genital track.

Figure 1:
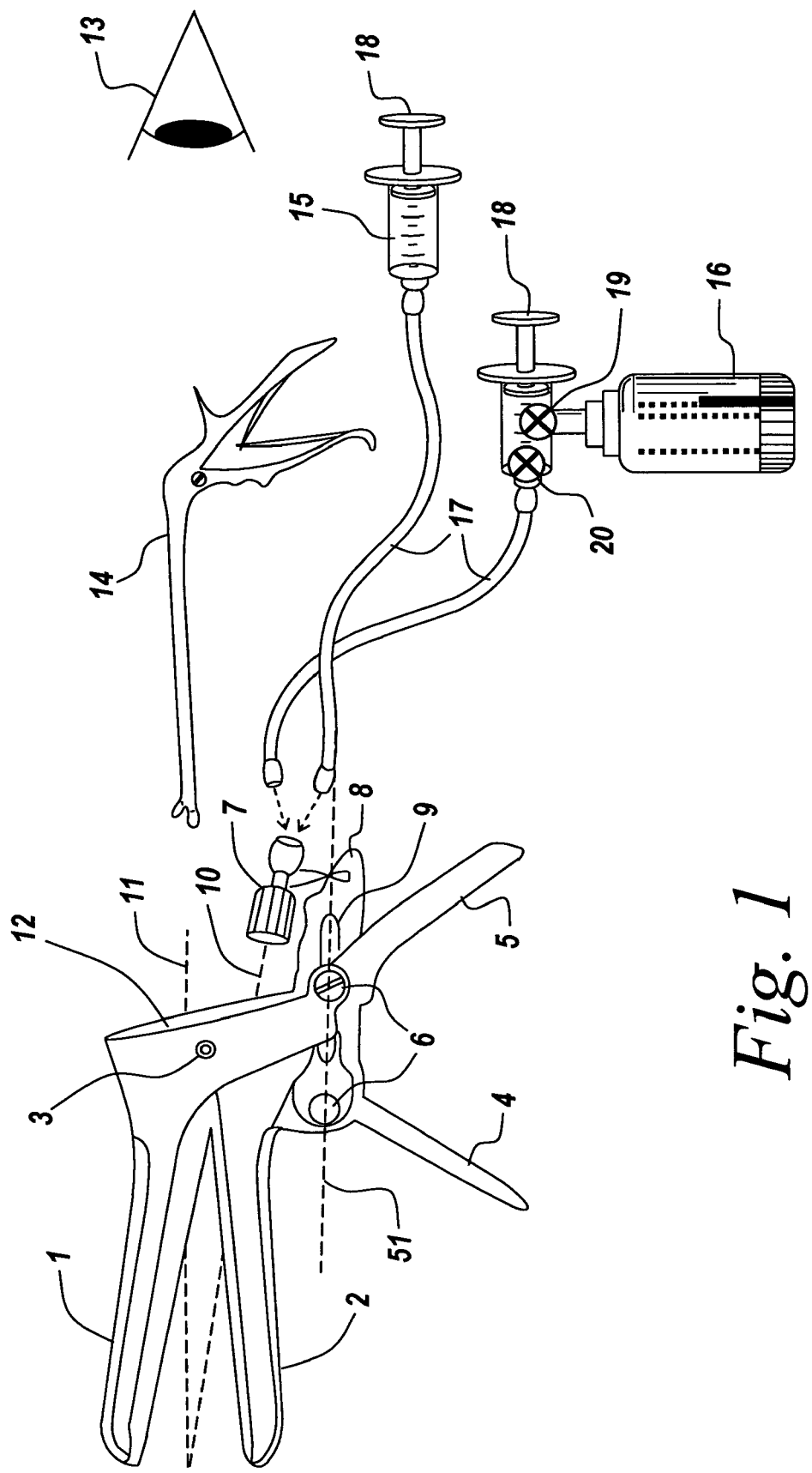
FIG. 1 illustrates a vaginal speculum arrangement composed by blades and handles, an extension rod mechanically coupled with the blades, and injection probe affixed onto the rod, a liquid marker container, and hydraulic means to enable injection of the marker.

FIG. 1 depicts a Cusco-type speculum having two blades (1, 2) connected to each other with the aid of a pivoting joint (3), located at the rear part of the blades. Each blade is movably coupled with the corresponding handle (4, 5) with the aid of a pin (6). The separation distance between the handles (4, 5) becomes maximum when the front parts of the blades (1, 2) are in contact. When the speculum is inserted into the vagina, the blades are in or near contact to each other, for the patient's comfort. After insertion, the handles (4, 5) are approached to each other, separating the blades (1, 2) and opening the vagina. The blade separation is mechanically locked at a desirable position, determined by the anatomy of the tissue. Then the examination follows involving the application of one or more diagnostic markers and the monitoring of the marker-induced alterations in the properties, e.g., the color, of the tissue. As it has been stated above, the uniform application of a standardized quantity of the diagnostic marker, while simultaneously allowing for the tissue inspection is critical for examination and diagnostic evaluation.

Uniform and simultaneous application of the marker over the entire area of the examined tissues can be achieved with the aid of a liquid injection mechanism, capable of dispensing the marker from a distance. In the case that the cervix of the uterus is examined, and because of its almost circular shape, a preferable injection pattern is conical with a maximum diameter equal with the diameter of the cervix, which is approximately 2.5-3 cm (1 inch).

An injection probe (7) is preferably mounted properly onto a fixed position, so that its injection direction is not affected by the opening angle of the speculum blades (1, 2), which may vary due to the anatomy of the vagina. Such a fixed position cannot be achieved by affixing the injection probe (7) on any of the blades, since by changing their angle the injection direction will change accordingly. Consequently, depending on the blade angle different parts of the tissue will be exposed to a different volume of the marker fluid.

In the case of a Cusco-type speculum the blades open symmetrically around the speculum's pivoting joint (3), thus composing an eligible mount to affix the injection probe (7). Another solution, comprising another embodiment of the present invention is to affix the injection probe (7) onto an extension shaft (8), which is mechanically coupled with the pins (6) connecting the handles with the blades. The front part of the shaft is movably coupled with the blade-handle joint of the first blade (4), while the pin of the blade-handle joint of the second blade (5) can slide within a groove (9), formed along the longitudinal axis (51) of the extension shaft (8). This arrangement ensures that the relative position of the longitudinal axis (10) of the injection probe (7) with the longitudinal symmetry axis (11) of the blade system remains the same for all possible blade angles. The longitudinal symmetry axis (11) discussed herein refers to a longitudinal axis about which the first blade (1) and the second blade (2) exhibit symmetry. Therefore, by properly mounting the injection probe (7) onto the extension shaft (8), the longitudinal axis (10) of the injection probe (7) intersects the central area of the examined tissue in all possible relative positions of the blades (1, 2), thus ensuring uniform application of the marker in various anatomic conditions.

In one embodiment of the present invention, the injection probe (7) is a nozzle remotely delivering a mist of liquid marker droplets of a desirable size onto the surface of the tissue. The cross section of the injection probe (7) is substantially smaller that the rear opening of the blade system (12) and preferably it has a needle nozzle-like shape for the purpose of not obscuring the visualization (13) of the tissue before, during and after injection and for allowing for the insertion of treatment tools (14). The liquid marker is transmitted to the injection probe (7) from a marker container (15, 16) either by permanently or detachably connecting these parts to each other, or through a tube (17) connecting these parts either permanently or detachably. The injection of the fluid is achieved with the aid of hydraulic pressure manually or otherwise applied.

In one embodiment of the present invention, the container and the hydraulic means comprise a syringe with a container (15) and a piston (18). In another embodiment of the present invention, the container is bottle (16) and the hydraulic means is a tube with two one-way valves (19) and a piston (18). When the piston (18) is pulled out, the liquid fills-up the tube enclosing the piston with a desirable quantity of marker liquid and the valve of the bottle (19) closes. By pushing the piston in, the tube valve (20) opens, the bottle valve (19) closes and the liquid is injected from the injection probe (7). In one embodiment of the invention, more than one marker staining different features of diagnostic performance is performed with the arrangement described above either simultaneously or in time sequence.

Clinical investigations conducted by the inventors of the present invention have shown that the optimum quantity of the marker is a volume of between about 2.5 ml and 3.5 ml. This volume ensures a sufficient and uniform washing of the entire surface of the cervix to produce the diagnostic optical effect. At the same time, this volume is desirable, since it eliminates unwanted accumulation of marker in excess between the lower blade (2) and the lower part of the examined tissue, which may obscure the visualization of the tissue.

The vaginal speculum arrangement of the present invention, as illustrated in FIG. 1, may be manufactured either in part or in whole either from metallic or from synthetic (plastic, Plexiglas) material. The speculum arrangement of the present invention either in part or in whole, may be either re-usable or disposable. In one embodiment, the speculum arrangement comprising the blade and handle system, the extension shaft (8) onto which the injection probe (7) (e.g., a nozzle) is affixed, the injection probe (7) mechanically coupled with the syringe pre-filled with the marker, is disposable.

Figure 2:
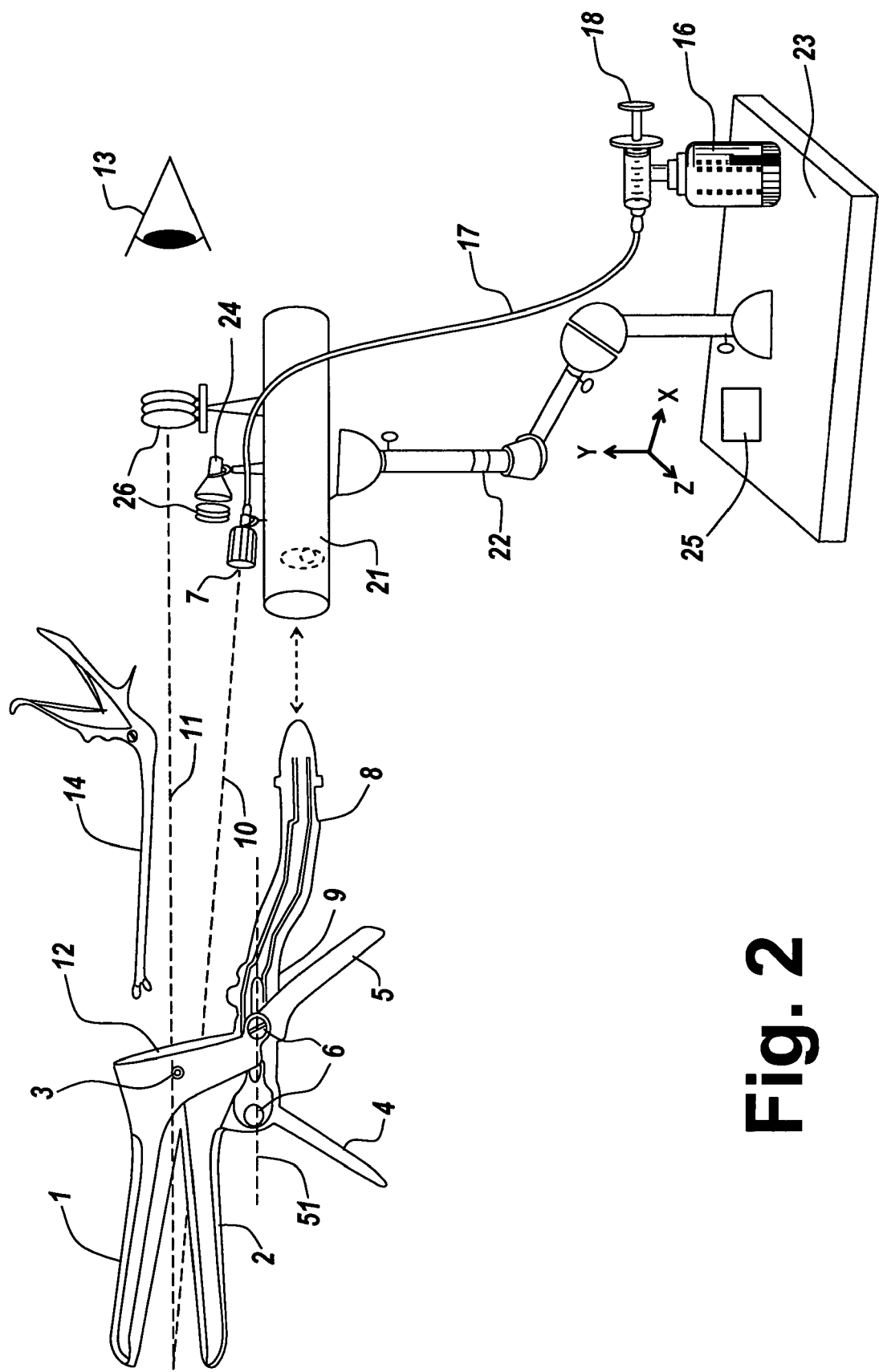
FIG. 2 illustrates a vaginal speculum arrangement composed of blades and handles, an extension rod mechanically coupled with the blades, and a mechanical support attached to a platform such as the ground or to the examination bed and connected detachably with the extension shaft. Onto the mechanical support and in the vicinity of its connection point with the extension shaft, the following components are mounted: an injection probe, a light source with a removable polarizer and removable rotating imaging polarizer, optical filter means and image magnifying optics.

FIG. 2 depicts another embodiment of the vaginal speculum arrangement. The vaginal speculum arrangement includes an extension shaft (8). The length of the extension shaft (8) is determined by the working distance of an optical imaging apparatus employed for the examination the lower part of woman's genital system, such as cameras, colposcopes etc. and combinations thereof. The extension shaft (8) is detachably connected with these imaging apparatuses, with the aid of a locking mechanism (21). The locking mechanism (21) is affixed onto the imaging apparatus and at a proper location so that when the locking mechanism is coupled with the extension shaft (8), the longitudinal symmetry axis (11) of the blade system coincides substantially with the bisector of the viewing angle (13). In another embodiment of this invention, suitable for speculoscopy use, the locking mechanism (21) is mounted on a mechanical support, which in turn is either affixed onto the examination bed or includes a base (23) placed on the ground. The mechanical support may be an articulating arm (22) to facilitate manipulations for the connection of the speculum shaft (8) with the locking mechanism (21).

The following components may be mounted onto the mechanical support (22) in the vicinity of the mechanical support's (22) connection point with the extension shaft (8): an injection probe (7), connected with a marker container (16, 15) either directly or though a tube (17) and hydraulic means for enabling injection, all having the specifications described above with respect to FIG. 1, a light source (24) with a power supply (25) and at least one of the following optical elements (26) interposed in the illumination and imaging ray paths: magnifying and focusing optics, filters and polarizers. The optical elements (26) may be mounted in a removable manner from the path of the rays, by titling them left or right. The polarizers may be affixed on a mount allowing the rotation of their polarization axes.

The cross section of the light source and illumination optics (24, 26) is substantially smaller than the rear optical aperture of the blade system (12) for the purpose of not obscuring the visualization of the tissue.

The light source (24) may be a halogen lamp and/or a LED lamp or other suitable light source. When the polarization axis of the imaging polarizer becomes, after rotation, vertical with the polarization axis of the light source, then the surface reflection (glare) is eliminated, resulting in a substantial improvement of the perceived contrast. This facilitates the detection and monitoring of features of diagnostic importance. The perceived contrast is further enhanced with the aid of an optical filter and image magnifying means (26).

Once the extension shaft (8) is connected with the mechanical support, the longitudinal axis (10) of the injection probe (7) may have a fixed relative position with the longitudinal axis (11) of the blade system, ensuring that the former intersects the central area of the tissue and the uniform application of the marker onto the entire area of the examined tissue.

The vaginal speculum arrangement of the current invention, illustrated in FIG. 2, may be manufactured either in part or in total either from metallic or from synthetic (plastic, Plexiglas) material. The speculum arrangement of the current invention may be in part either re-usable or disposable. In one preferable embodiment of the vaginal arrangement as depicted in FIG. 2, the blade-handle system with the extension shaft (8) is disposable and the mechanical mount with the components (in part or in whole) mounted on it, is re-usable.

Figure 3:
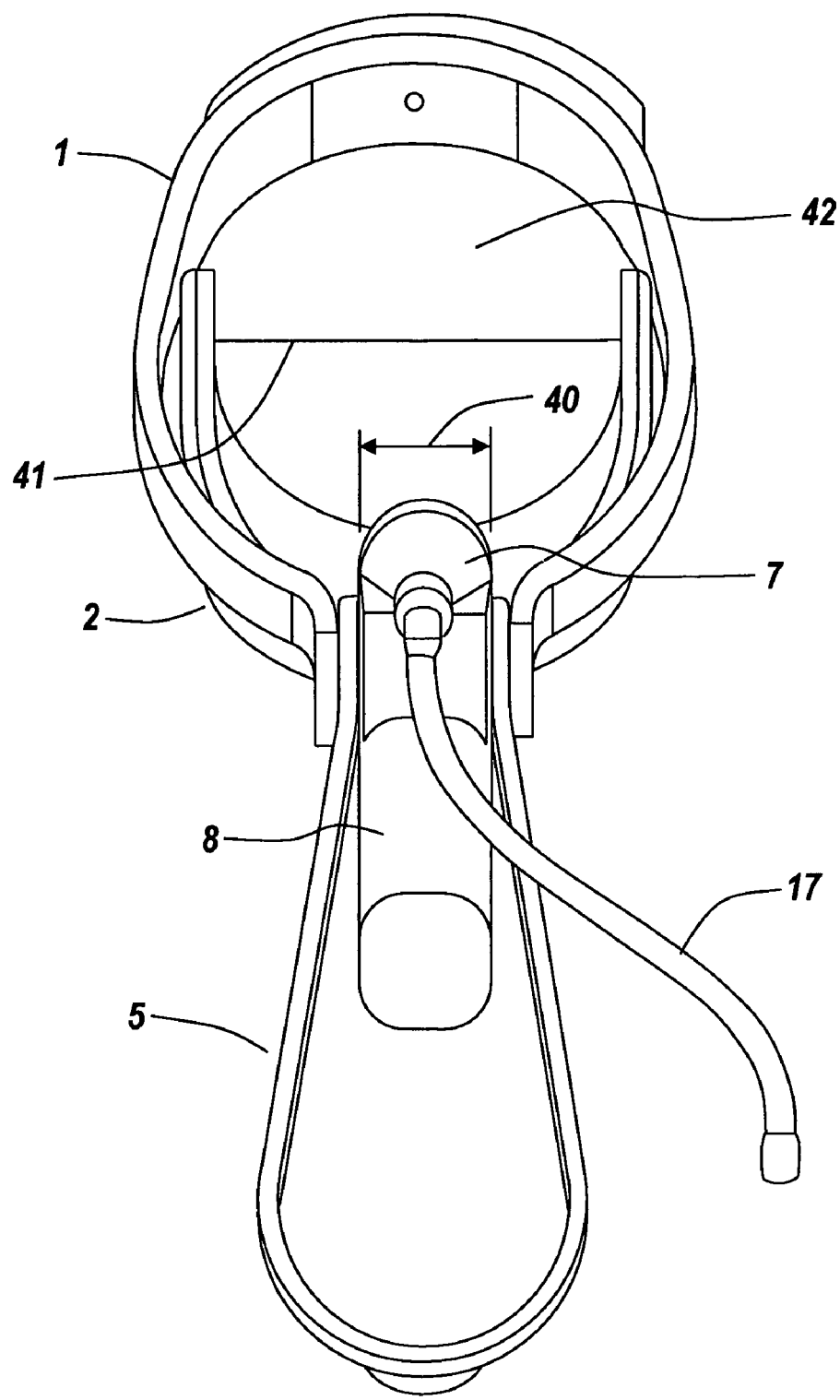
FIG. 3 illustrates a rear-view of a speculum in accordance with the teachings of the present invention.

FIG. 3 illustrates a rear-view of the joined speculum blades (1, 2), the extension shaft (8) and the injection probe (7) (e.g., a nozzle). The dimensions of the cross section (40) of the injection probe (7) is substantially smaller than the dimensions of the cross section (41) of a rear aperture (42) of the blade system, thus allowing for the visualization of the examined area before, during, and after the injection of the marker.

Figure 4:
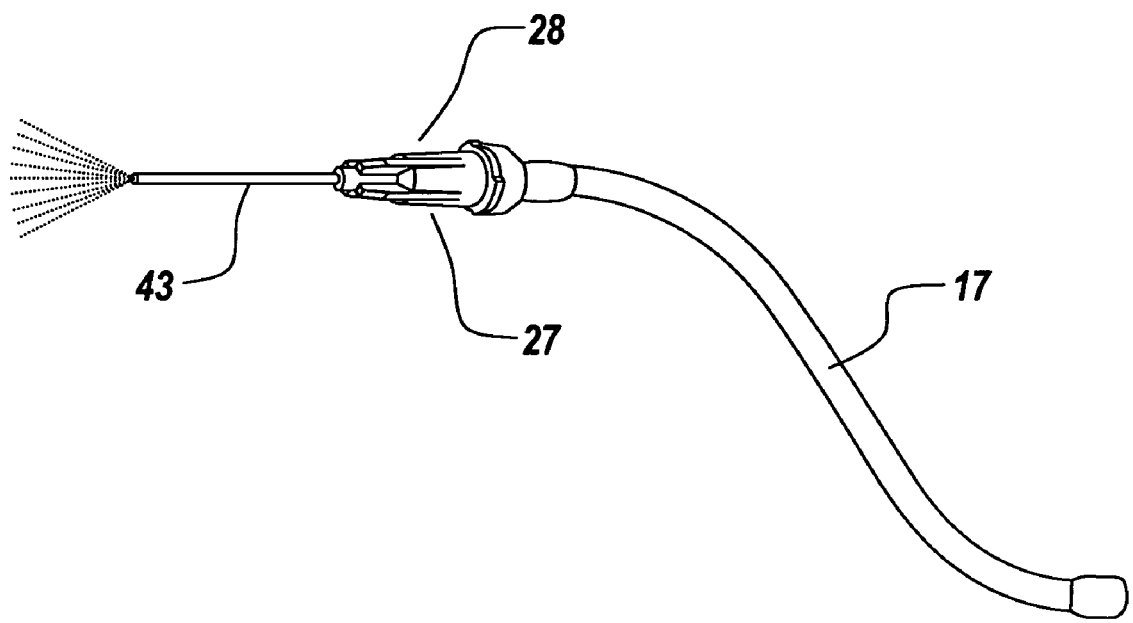
FIG. 4 illustrates a needle nozzle with a needle having an outside diameter sized to maximize the field-of-view through the rear aperture of a speculum in accordance with the teachings of the present invention. A coupling mechanism is used for connection of the needle nozzle with the tube providing a channel through which the marker flows.

FIG. 4 illustrates a needle nozzle (27), with the needle (43) having an outside diameter sized to maximize the field-of-view through the rear aperture (42) of the blade system. A coupling mechanism (28) is used for the connection of the needle nozzle (27) with the tube (17) providing a channel for the marker from a container holding to marker to an input orifice of the coupling mechanism (28).

Figure 5:
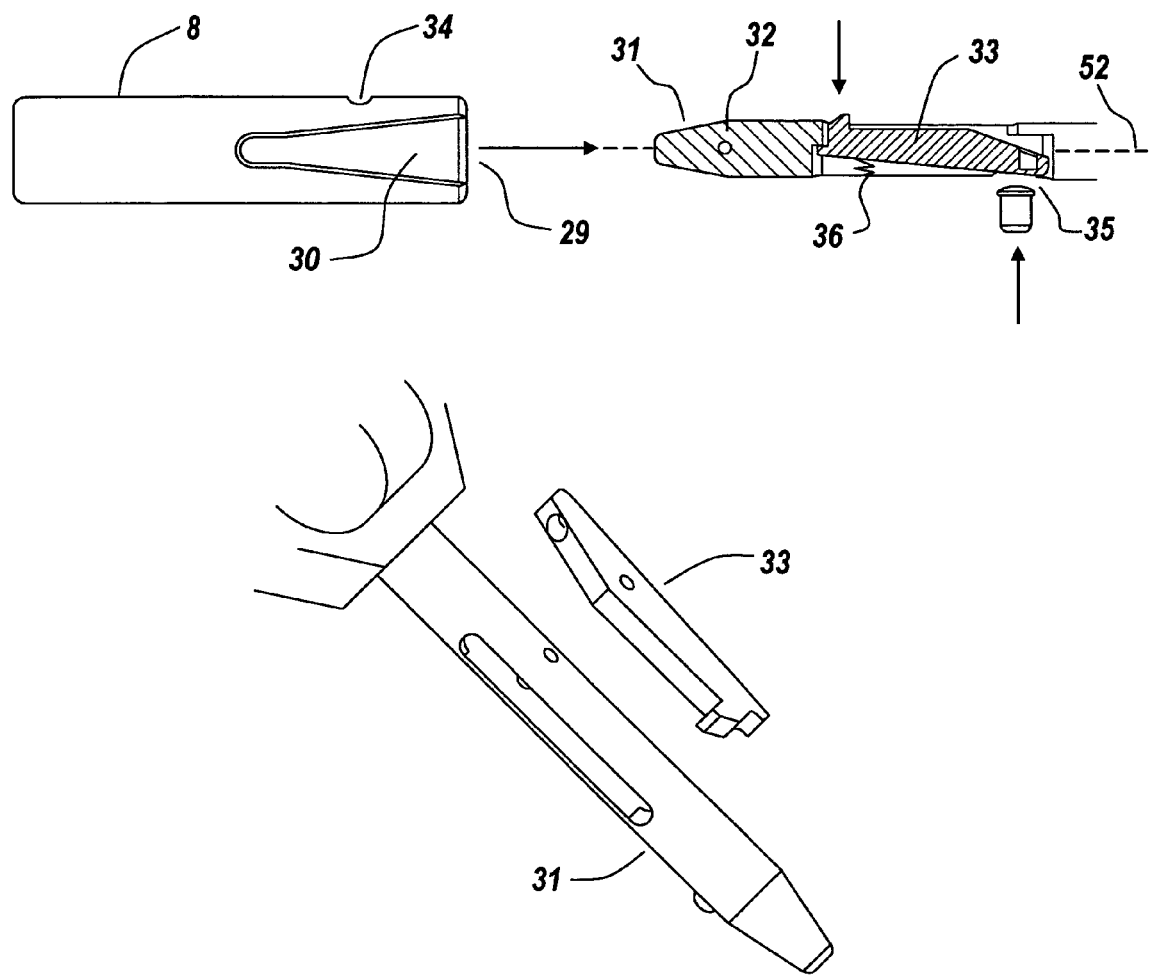
FIG. 5 illustrates an apparatus for securing a speculum shaft onto an optical imaging system, or onto a base member.

FIG. 5 illustrates one embodiment of the extension shaft (8) in more detail. Those skilled in the art will appreciate the extension shaft (8) is not limited to the embodiment illustrated and other shaft configurations are possible. The extension shaft (8) illustrated in FIG. 5 is well suited for use in securing the speculum shaft onto an optical imaging system (26), onto a base member (23), or both. In the illustrated embodiment, the distal end (29) of an extension shaft (8) includes a conically tapered slot (30) in a bottom side. The conically tapered slot (30) acts as a guide for the proper alignment of the speculum with respect to the external optical system (26). A securing mechanism engages with the distal end (29) of the extension shaft (8) with an extension pin (31) that has a dowel pin (32) having a longitudinal axis perpendicular to a longitudinal axis (52) of the extension pin (31). The position of the dowel pin (32) determines the displacement of the speculum from the external optical system. The distal end (29) of the shaft (8) engages with the extension pin (31) using a spring-loaded, cam action wedge (33). The distal end (29) of the shaft (8) also includes a receptacle slot (34) to mate with the cam action wedge (33).

In operation, the extension shaft (8) is moved towards the optical system to urge the dowel pin (32) into contact with the conically tapered groove in the extension shaft (8) until the cam action wedge (33) mates with the receptacle slot (34) in the extension shaft (8).

The extension shaft (8) is unlocked from the dowel pin (32) by pressing on a release button (35) which has the effect of engaging with the cam action wedge (33). In this state, the receptacle slot (34) is devoid of a locking member and the extension shaft (8) can be removed. The cam action wedge (32) and the release button (35) are returned to their normal states due to the action of the spring (36) housed in the engagement pin (31).

The invention claimed is:

1. A vaginal speculum arrangement comprising:
a blade system for opening the vagina, the blade system having a first blade and a second blade positionable relative to each other in a plurality of non-zero angles and along a longitudinal symmetry axis between a distal portion and a proximate portion of each of the first and second blades, said first blade and second blade connected to each other by a pivoting joint located at the rear of the blades, and
an injection mechanism for dispensing a diagnostic marker onto a surface of examined tissue, the injection mechanism having an injection probe having a longitudinal axis, a marker container and an injector for enabling injection of the marker, wherein the non-zero angle between the longitudinal axis of the injection probe and the longitudinal symmetry axis of the blade system remains substantially constant for each of the plurality of angles between the first and second blades,
a cross section of the injection probe having dimensions that are substantially smaller than dimensions of a cross section of a rear aperture of the blade system, and
wherein the injection probe allows for a substantially homogeneous application of the marker on a desired area of the examined tissue, irrespectively from an opening angle of the first and second blades and allows for observation of the desired area through the rear aperture of the blade system, before, during, and after the injection of the marker.

2. The vaginal speculum arrangement of claim 1 wherein the vaginal speculum arrangement further comprises:
a mechanical support having a shaft with a first shaft end mechanically coupled with the blade system and a second shaft end detachably coupled to the injection mechanism.

3. The vaginal speculum arrangement of claim 1, wherein the vaginal speculum arrangement further comprises:
a mechanical support having a shaft with a first shaft end mechanically coupled with the blade system and a second shaft end detachably coupled to one of a base member or an imaging apparatus.

4. The vaginal speculum arrangement of claim 1, further comprising a mechanical support having a shaft with a first shaft end mechanically coupled with the blade system and the injection probe mounts to a portion of the shaft.

5. The vaginal speculum arrangement of claim 4, wherein the first shaft end of said shaft is movably coupled with a blade-handle joint of the first blade, and a pin of the blade-handle joint of the second blade moves within a groove, formed along a longitudinal axis of said shaft.

6. The vaginal speculum arrangement of claim 2, wherein the first shaft end of said shaft is movably coupled with a blade-handle joint of the first blade, and a pin of the blade-handle joint of the second blade moves within a groove, formed along a longitudinal axis of said shaft.

7. The vaginal speculum arrangement of claim 2, wherein the base member includes an articulated arm with a first end portion affixed to a fixed position of the base member and a second end portion affixed to a locking mechanism of the shaft.

8. The vaginal speculum arrangement of claim 7, wherein said locking mechanism includes one of a mechanical locking mechanism, a magnetic locking mechanism, or an electro-magnetic locking mechanism.

9. The vaginal speculum arrangement of claim 8, wherein said injection probe is affixed to said mechanical base in a vicinity of said locking mechanism.

10. The vaginal speculum arrangement of claim 1, wherein said injection probe comprises a nozzle.

11. The vaginal speculum arrangement of claim 10, wherein said nozzle comprises a needle nozzle.

12. The vaginal speculum arrangement of claim 1, wherein the injection mechanism further comprises a hydraulic pump means for pumping a predetermined volume of a marker into and through said injection probe.

13. The vaginal speculum arrangement of claim 12, wherein said predetermined volume of the marker ranges between about 2.5 ml and about 3.5 ml.

14. The vaginal speculum arrangement of claim 12, wherein said marker is between about 3% and about 5% acetic acid solution.

15. The vaginal speculum arrangement of claim 1, further comprising a light source.

16. The vaginal speculum arrangement of claim 7, further comprising a light source affixed to the base member in a vicinity of said shaft locking mechanism.

17. The vaginal speculum arrangement of claim 1, further comprising an optical element.

18. The vaginal speculum arrangement of claim 17, wherein the optical element comprises one of a magnifying optical element, a focusable optical element, an optical filter or a pair of polarizers, wherein one of said polarizers is provided for polarizing light emitted by the light source and one of said polarizers is provided for polarizing light reflected by the tissue under observation, the polarizers having their polarization axes perpendicular to each other.

19. The vaginal speculum arrangement of claim 2, wherein said blade system, said shaft and said injection probe are formed from a metallic material.

20. The vaginal speculum arrangement of claim 19, wherein said blade system, said shaft and said injection probe are re-usable.

21. The vaginal speculum arrangement of claim 2, wherein said blade system, said shaft and said injection means each have a portion formed from a polymeric compound.

22. The vaginal speculum arrangement of claim 21, wherein said blade system, said shaft and said injection means are disposable.

23. A vaginal speculum arrangement comprising:
a blade system for opening the vagina, the blade system having a first blade and a second blade being positionable relative to each other in a plurality of non-zero angles and along a longitudinal symmetry axis between a distal portion and a proximate portion of each of the first and second blades, said first blade and second blade connected to each other by a pivoting joint located at the rear of the blades; and
a mechanical support having a shaft with a first shaft end mechanically coupled with the blade system and a second shaft end detachably coupled to another device, wherein said first shaft end of said shaft is movably coupled with a blade-handle joint of the first blade, and a pin of the blade-handle joint of the second blade moves within a groove, formed along a longitudinal axis of said shaft.

24. The vaginal speculum arrangement of claim 23, wherein said other device is an injection mechanism for dispensing a diagnostic marker onto the surface of an examined tissue.

25. The vaginal speculum arrangement of claim 23, wherein said other device is an imaging apparatus.

26. The vaginal speculum arrangement of claim 23, wherein said other device is a base member.

27. The vaginal speculum arrangement of 24, wherein said injection mechanism for dispensing a diagnostic marker onto the surface of the examined tissue has an injection probe having a longitudinal axis, a marker container and injector for enabling injection of the marker, wherein the relative position of the longitudinal axis of the injection probe and the longitudinal symmetry axis of the blade system remain substantially fixed for each of the plurality of angles between the first and second blades, wherein a cross section of the injection probe has dimensions that are substantially smaller than dimensions of a cross section of a rear aperture of the blade system, and the injection probe allows for a substantially homogeneous application of the marker on a desired area of the examined tissue, irrespectively from an opening angle of the first and second blades and allows for observation of the desired area through the rear aperture of the blade system, before, during, and after the injection of the marker.

28. The vaginal speculum arrangement according to claim 27, wherein the injection probe mounts to a portion of said mechanical support's shaft.

29. The vaginal speculum arrangement of claim 26, wherein said base member includes an articulated arm with a first end portion affixed to a fixed position and a second end portion affixed to a locking mechanism of the shaft.

30. The vaginal speculum arrangement of claim 27, wherein said injection probe comprises a nozzle.

31. The vaginal speculum arrangement of claim 24, characterized by the fact that the injection mechanism further comprises a hydraulic pump means for pumping a predetermined volume of a marker into and through said injection probe.

32. A vaginal speculum arrangement comprising: a blade system for opening the vagina, the blade system having a first blade and a second blade positionable relative to each other in a plurality of non-zero angles and along a longitudinal symmetry axis between a distal portion and a proximate portion of each of the first and second blades, said first blade and second blade connected to each other by a pivoting joint located at the rear of the blades;
an injection mechanism for dispensing a diagnostic marker onto a surface of examined tissue, the injection mechanism having an injection probe having a longitudinal axis, a marker container and an injector for enabling injection of the marker, wherein the non-zero angle between the longitudinal axis of the injection probe and the longitudinal symmetry axis of the blade system remains substantially constant for each of the plurality of angles between the first and second blades, a cross section of the injection probe having dimensions that are substantially smaller than dimensions of a cross section of a rear aperture of the blade system, and wherein the injection probe allows for a substantially homogeneous application of the marker on a desired area of the examined tissue, irrespectively from an opening angle of the first and second blades and allows for observation of the desired area through the rear aperture of the blade system, before, during, and after the injection of the marker;

a mechanical support having a shaft with a first shaft end mechanically coupled with the blade system and a second shaft end detachably coupled to the injection mechanism, wherein the first shaft end of said shaft is movably coupled with a blade-handle joint of the first blade, and a pin of the blade-handle joint of the second blade moves within a groove, formed along a longitudinal axis of said shaft.

* * * * *